US011234671B2

(12) United States Patent
Kawabata et al.

(10) Patent No.: US 11,234,671 B2
(45) Date of Patent: Feb. 1, 2022

(54) ULTRASONIC DIAGNOSTIC APPARATUS

(71) Applicant: Konica Minolta, Inc., Tokyo (JP)

(72) Inventors: Akihiro Kawabata, Hachioji (JP); Shinya Kurokawa, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 1168 days.

(21) Appl. No.: 15/712,286

(22) Filed: Sep. 22, 2017

(65) Prior Publication Data

US 2018/0085087 A1 Mar. 29, 2018

(30) Foreign Application Priority Data

Sep. 28, 2016 (JP) .............................. JP2016-189882

(51) Int. Cl.
*A61B 8/06* (2006.01)
*A61B 8/08* (2006.01)
*A61B 8/00* (2006.01)
*A61B 8/14* (2006.01)

(52) U.S. Cl.
CPC .............. *A61B 8/06* (2013.01); *A61B 8/5269* (2013.01); *A61B 8/14* (2013.01); *A61B 8/462* (2013.01); *A61B 8/463* (2013.01); *A61B 8/56* (2013.01)

(58) Field of Classification Search
CPC ........... A61B 8/06; A61B 8/5269; A61B 8/14; A61B 8/462; A61B 8/463; A61B 8/56
See application file for complete search history.

(56) References Cited

U.S. PATENT DOCUMENTS

| 5,188,113 A * | 2/1993 | Sato ......................... A61B 8/06 600/441 |
| 5,897,502 A * | 4/1999 | Wong ................... G01S 7/52034 600/454 |
| 7,044,913 B2 * | 5/2006 | Shiki ....................... A61B 8/06 600/437 |

(Continued)

FOREIGN PATENT DOCUMENTS

| JP | H02-286140 A | 11/1990 |
| JP | 5652395 B2 | 11/2014 |

*Primary Examiner* — Pascal M Bui Pho
*Assistant Examiner* — Sean A Frith
(74) *Attorney, Agent, or Firm* — Lucas & Mercanti, LLP

(57) ABSTRACT

An ultrasonic diagnostic apparatus, including a transceiver for sequentially generating multiple received signals, a color flow mapping signal processing unit that generates blood flow velocity data based on the multiple received signals, and a residual image processing unit that includes an aliasing determination unit and a persistence calculation unit and performs residual image processing on blood flow velocity data, an aliasing determination unit that adds the blood flow velocity data $V_{current}$ for the most recent frame and the blood flow velocity data $V_{out-1}$ for the frame preceding the most recent frame, performs aliasing determination on the frame that was determined by a frame before the most recent frame based on the aliasing determination results of the blood flow velocity data, and a persistence calculation unit that performs a persistence calculation after performing a correction to the blood flow velocity data in which aliasing has occurred.

7 Claims, 10 Drawing Sheets

(56) References Cited

U.S. PATENT DOCUMENTS

| | | | |
|---|---|---|---|
| 8,435,182 B1* | 5/2013 | Tamura | G01S 15/8986 600/454 |
| 2009/0062650 A1* | 3/2009 | Miyaki | A61B 8/13 600/443 |
| 2012/0101384 A1* | 4/2012 | Migita | A61B 8/06 600/443 |

* cited by examiner

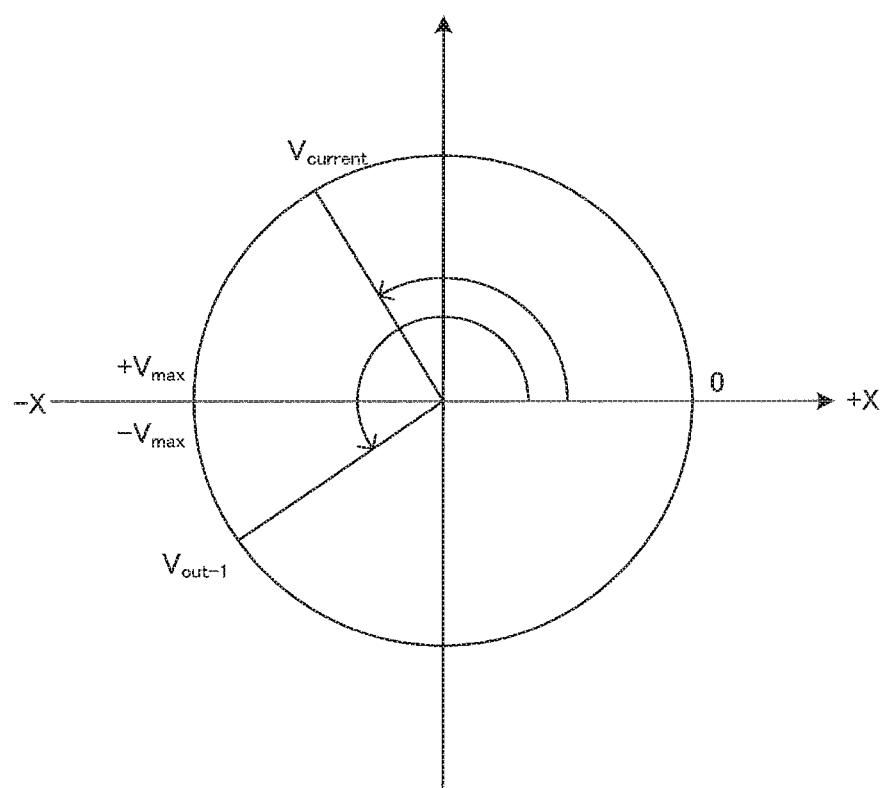

ULTRASONIC DIAGNOSTIC APPARATUS

CROSS-REFERENCE TO RELATED APPLICATIONS

Japanese Patent Application No. 2016-189882 filed on Sep. 28, 2016 including description, claims, drawings, and abstract the entire disclosure is incorporated herein by reference in its entirety.

BACKGROUND

Technological Field

The present invention relates to an ultrasonic diagnostic apparatus for performing residual image processing during color flow mapping.

Description of the Related Art

Ultrasonic diagnostic apparatuses transmit ultrasonic waves to a subject and analyze information included in the reflected echoes to create an image of the subject. Due to a technique called Color Flow Mapping (hereinafter sometimes abbreviated as CFM), given its capability to image blood flow in subjects, use of ultrasonic diagnostic apparatuses that can image blood flow have become widespread in all fields of medicine.

Color flow mapping is also called Color Doppler Imaging (CDI) and is a technique that uses the Doppler Effect. When ultrasonic waves irradiate blood flow, a Doppler shift occurs in the reflected echo in proportion to the blood flow velocity due to the Doppler Effect. Information on this Doppler shift is detected by orthogonal detection and subjected to a high-pass filter called an MTI (Moving Target Indicator) filter, auto-correlation processing and noise filtering, thereby obtaining information on blood flow velocity. Information obtained on blood flow velocity is converted into color information and superimposed on a B-mode tomographic image (an image representing the amplitude of the echoes as luminance) two-dimensionally, whereby blood flow in the subject can be suitably displayed.

Received signal intensities based on the reflected echoes from blood flow is small compared to received signal intensities of reflected echoes from tissue scatterers and tissue boundaries used for generating B-mode tomographic images. Therefore, blood flow velocity and blood flow power (moving blood flow velocity) obtained by signal processing in color flow mapping tend to be unstable.

Particularly when the blood flow velocity of the portion to be observed is slow or when the portion to be observed is a peripheral blood vessel, the blood flow power becomes small, so in the process of noise filtering, which should primarily filter out system noise and acoustic noise, there is a tendency for information on blood flow velocity or blood flow power to be removed. As a result, a phenomenon occurs in which a portion which is primarily displayed as blood flow in the blood flow image is darkened. Specifically, for example, when blood flow in the subject is imaged at a rate of several frames to several tens of frames per second, the blood flow portion is displayed in black in some of the frames. For this reason, the blood flow portion in the tomographic image suddenly disappears, and the image becomes unnatural or lacks smoothness.

As an ultrasonic diagnostic apparatus that solves such a problem, an ultrasonic diagnostic apparatus that performs time direction interpolation called persistence processing (residual image processing) in the post-signal processing stage is disclosed in, for example, JP 02-286140 A. An example of a specific configuration of a ultrasonic diagnostic apparatus that performs persistence processing will be briefly described below.

In the existing ultrasonic diagnostic apparatus shown in FIG. 8, the ultrasonic transceiver unit 402 drives the probe 401 and transmits ultrasonic waves to the subject. In addition, the probe 401 receives the reflected echo generated in the subject and generates a reception signal. When generating a B-mode tomographic image, the ultrasonic transceiver unit 402 performs transmission/reception suitable for generating a B-mode tomographic image and outputs the obtained reception signal to the tomographic image signal processing unit 409. When generating a color flow mapping tomographic image, transmission and reception suitable for generating a color flow mapping tomographic image are performed, and the obtained received signal is outputted to a color flow mapping processing unit 403 (hereinafter, abbreviated as a CFM signal processing unit). Generally, when generating a color flow mapping tomographic image, in order to obtain a stable color flow mapping tomographic image, the ultrasonic transceiver unit 402 performs transmission and reception of ultrasonic waves on the same acoustic line multiple times.

The CFM signal processing unit 403 performs orthogonal detection processing, MTI filtering, and auto-correlation processing on the received signal, calculates blood flow velocity and blood flow power, then performs noise filtering to eliminate system noise or acoustic noise, and outputs blood flow velocity and blood flow power to the frame memory unit 404.

The frame memory unit 404 is configured by a ring buffer, and stores the blood flow velocity and blood flow power, frame by frame, from the current scan frame to N frames before the current frame (where N is an integer equal to or greater than 1). Here, the frame shows the blood flow velocity and blood flow power data configuring the CFM tomographic image of one screen.

The frame memory selection unit 405 selects multiple pieces of CFM frame data set in advance from the frame memory unit 404 and outputs a command to the frame memory unit 404 to output the data to the persistence calculation unit 407. The persistence calculation unit 407 performs a persistence calculation based on the CFM frame data read from the frame memory unit 404 and the persistence coefficient output from the persistence coefficient setting unit 406, and outputs the result to a CFM DSC (Digital Scan Converter) unit 408. The persistence calculation is a simple weighting operation, and the persistence coefficient output from the persistence coefficient setting unit 406 is a fixed coefficient set in advance from the system. The persistence calculation is an operation that yields a residual image by performing a weighted addition on images of the current and of a plurality of consecutive frames and displaying the results.

The CFM DSC unit 408 converts the coordinates of the CFM frame data output from the persistence calculation unit 407, and outputs it to the image combining unit 411.

The tomographic image signal processing unit 409 performs dynamic filtering on the received signal to eliminate unnecessary noise and then applies envelope detection and dynamic range compression and outputs the tomographic image frame data to the tomographic image DSC unit 410. The tomographic image DSC unit 410 converts the coordinates of the tomographic image frame data from the tomographic image signal processing unit 409 and outputs it to the image combining unit 411.

The image combining unit 411 combines frame data output from the CFM DSC unit 408 and the tomographic image DSC unit 410 for each pixel to generate combined image frame data. Specifically, when blood flow velocity is zero, tomographic image frame data is displayed. Otherwise, two pieces of data for each pixel or data for each corresponding measurement point are combined such that the CFM frame data is displayed. In addition, the tomographic image DSC unit 410 converts data into color information according to the blood flow velocity and direction of blood flow, and outputs it to the display 412. The display 412 displays the data received from the image combining unit 411.

SUMMARY

Blood flow velocity that can be measured by the Doppler shift is restricted by the pulse repetition frequency (PRF). As a result, aliasing, which is a phenomenon in which the blood flow velocity corresponding to the frequency change exceeding ±PRF/2 is observed as blood flow velocity in the opposite direction, occurs and it becomes difficult to accurately evaluate the blood flow velocity.

When aliasing occurs as described above, in order to obtain a good image, it is necessary to determine whether or not aliasing has occurred and correct for the effect. As a technique for detecting and correcting for the occurrence of aliasing, there is a technique disclosed in, for example, Japanese Patent No. 5652395. In Japanese Patent No. 5652395, after persistence coefficients to be used for persistence processing are dynamically set based on blood flow velocity and aliasing status, a persistence calculation is performed on CFM frame data. Thus, a technique is disclosed for correcting the image for the effect of aliasing. However, there is a desire to further improve the accuracy of determining whether or not aliasing has occurred.

To achieve at least one of the abovementioned objects, according to an aspect of the present invention, an ultrasonic diagnostic apparatus, reflecting one aspect of the present invention, comprises: a transceiver that transmits ultrasonic waves by driving a probe repeatedly, receives echoes reflected off a subject, and successively generates a plurality of received signals; a color flow mapping signal processing unit that successively generates blood flow velocity data of blood flow in the subject for each frame based on the plurality of received signals; a residual image processing unit that performs residual image processing on blood flow velocity of the each frame. The residual image processing unit includes; an aliasing determination unit that determines whether or not aliasing occurs in a first blood flow velocity data, being blood flow velocity data for a most recent frame, and in a second blood flow velocity data, being blood flow velocity data for a frame before the most recent frame with being subjected to the residual image processing, in which the determination is performed based on the first blood flow velocity data, the second blood flow velocity data, and a first aliasing determination result, being determined for the frame before the most recent frame and indicating presence or absence of aliasing in the blood flow velocity data for the frame with being subjected to the residual image processing, the aliasing determination unit further outputting a second aliasing determination result that is an aliasing determination result of the first blood flow velocity data, and a third aliasing determination result that is an aliasing determination result of the second blood flow velocity data, and a persistence calculation unit that, based on the second and third aliasing determination results and a predetermined persistence coefficient for adjusting the residual image effect, performs a persistence calculation using the first blood flow velocity data and the second blood flow velocity data, outputs a persistence calculation result as a third blood flow velocity data for the most recent frame that is the blood flow velocity data with being subjected to residual image processing, determines whether or not aliasing occurs in the third blood flow velocity data, and outputs data which is a fourth aliasing determination result.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

FIG. 2 is a schematic diagram illustrating the blood flow velocity and blood flow direction obtained based on the Doppler Effect;

DETAILED DESCRIPTION OF EMBODIMENTS

Hereinafter, one or more embodiments of the present invention will be described with reference to the drawings. However, the scope of the invention is not limited to the disclosed embodiments.

First Embodiment

Example Configuration of the Ultrasound Diagnostic Apparatus

Figure 1:
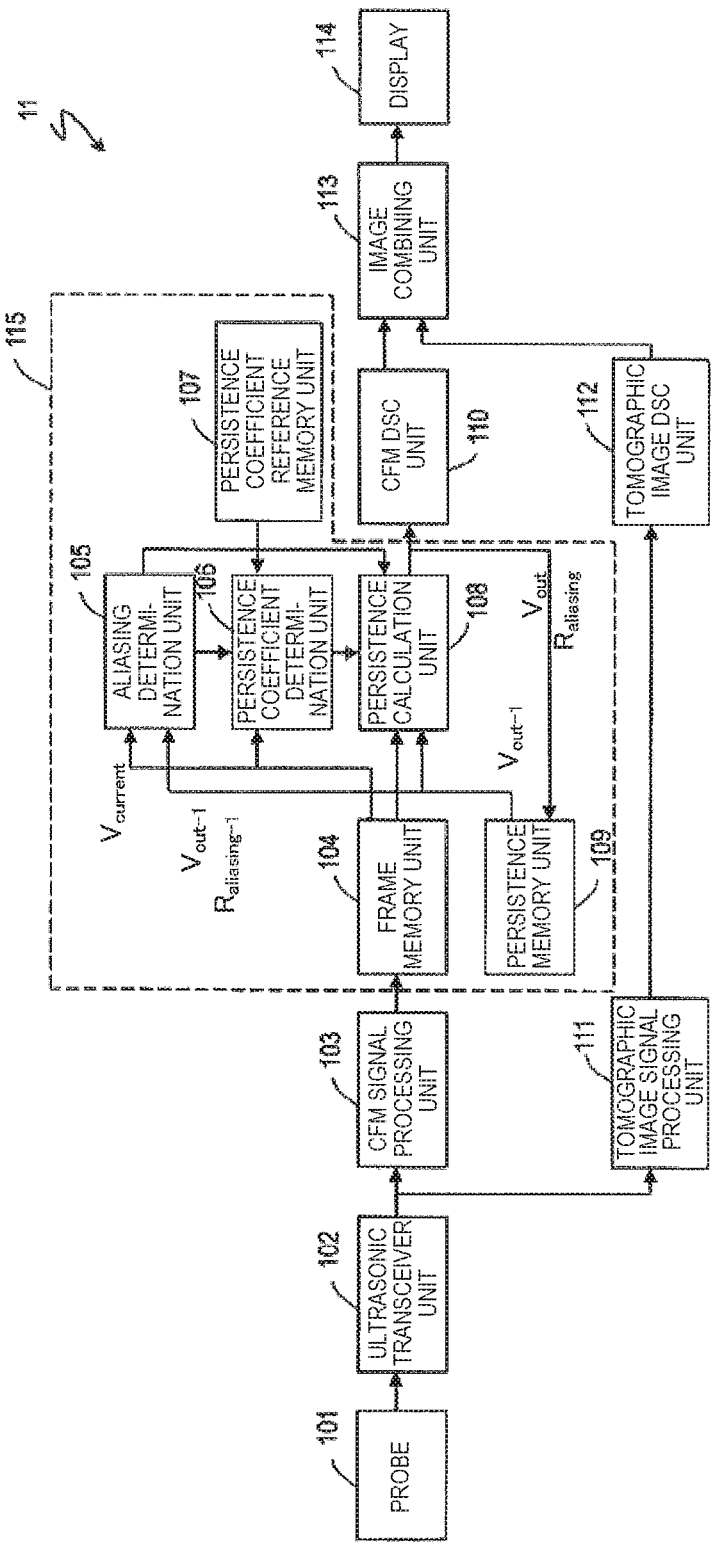
FIG. 1 is a block diagram showing an example configuration of an ultrasonic diagnostic apparatus according to the first embodiment of the present invention.

Hereinafter, an ultrasonic diagnostic apparatus according to the first embodiment of the present invention will be described with reference to the drawings. FIG. 1 is a block diagram showing an example configuration of an ultrasonic diagnostic apparatus according to the first embodiment of the present invention.

The ultrasonic diagnostic apparatus 11 shown in FIG. 1 includes a probe 101, an ultrasonic transceiver unit 102, a CFM signal processing unit 103, a residual image processing unit 115, a tomographic image signal processing unit 111, a CFM DSC unit 110, a tomographic image DSC unit 112, an image combining unit 113, and a display 114. Among these configurations, it is possible to use a general-purpose probe and a display device for the probe 101 and display 114, which is not necessary for the ultrasonic diagnostic apparatus 11 to include the probe 101 and display 114.

The ultrasonic transceiver unit 102 generates a drive signal for driving the probe 101 and outputs it to the probe 101. In response to this, the probe 101 transmits ultrasonic waves toward the subject. The probe 101 receives the reflected echo of the transmitted ultrasonic waves reflected off of the subject and generates reception signals. The ultrasonic transceiver unit 102 corresponds to the ultrasonic transceiver unit of the present invention.

More specifically, the probe 101 includes multiple piezoelectric elements, and ultrasonic waves are transmitted from each piezoelectric element. An ultrasonic beam is formed by ultrasonic waves transmitted from multiple piezoelectric elements. The ultrasonic transceiver unit 102 drives the probe 101 while performing delay control of each piezoelectric element so as to scan the subject with multiple ultrasonic beams.

Reflected echos from the subject are received by each piezoelectric element. The ultrasonic transceiver unit 102 has the probe 101 generate a reception signal that corresponds to the transmitted ultrasonic beam by controlling the delay of each piezoelectric element. When the ultrasonic beam scans the subject once, data for one frame is obtained. The probe 101 can sequentially generate reception signals of several frames to several tens of frames per second by scanning the subject several times to several tens of times per second.

The ultrasonic diagnostic apparatus 11 according to the first embodiment generates a B-mode tomographic image and a color flow mapping image, combines them, and displays them on the display 114. Therefore, the transmission and reception of ultrasonic waves with the ultrasonic transceiver unit 102 is performed for generating both the B-mode tomographic image and color flow mapping image. The number of frames per second of the B-mode tomographic image and the number of frames per second of the color flow mapping image may be the same or different. When the number of frames is the same, transmission and reception of ultrasonic waves for B-mode tomographic image generation and transmission and reception of ultrasonic waves for color flow mapping image generation may be alternately repeated.

When generating a B-mode tomographic image, the ultrasonic transceiver unit 102 performs transmission and reception suitable for generating a B-mode tomographic image and outputs the obtained reception signal to the tomographic image signal processing unit 111. On the other hand, when generating a color flow mapping tomographic image, the ultrasonic transceiver unit 102 performs transmission and reception suitable for generating a color flow mapping tomographic image and outputs the obtained reception signal to the CFM signal processing unit 103. Generally, when generating a color flow mapping tomographic image, in order to obtain a stable color flow mapping tomographic image, the ultrasonic transceiver unit 102 performs transmission and reception of ultrasonic waves on the same acoustic line multiple times.

The CFM signal processing unit 103, after performing orthogonal detection processing, MTI filtering, and auto-correlation processing on the received signal, calculates blood flow velocity and blood flow power, and then performs noise filtering to eliminate system or acoustic noise, and generates CFM frame data. CFM frame data includes at least blood flow velocity data and may also include blood flow power data and dispersion data of the blood flow velocity. The CFM signal processing unit 103 repeats the process for each received signal forming each frame. CFM frame data generated by the CFM signal processing unit 103 is output to the residual image processing unit 115 for each frame. The CFM signal processing unit 103 corresponds to the color flow mapping signal processing unit of the present invention.

The residual image processing unit 115, using the persistence coefficient, performs residual image processing on the CFM frame data for each frame. In the ultrasonic diagnostic apparatus 11 according to the first embodiment, the residual image processing unit 115 sets the persistence coefficient according to the blood flow velocity of the most recent frame. In other words, the persistence coefficient is not constant and is a dynamic value based on the blood flow velocity of the most recent frame. As a result, the persistence coefficient can be changed according to the blood flow velocity, and the residual image effect can be adjusted. However, blood flow velocity that can be measured by Doppler shift is restricted by the pulse repetition frequency (PRF). As a result, aliasing, which is a phenomenon in which the blood flow velocity corresponding to the frequency change exceeding ±PRF/2 is observed as blood flow velocity in the opposite direction, occurs and it becomes difficult to accurately evaluate the blood flow velocity. Therefore, the residual image processing unit 115 determines whether or not aliasing is occurring, and if it is determined that aliasing is occurring, corrects the blood flow velocity data, thereby, canceling the effect of the aliasing. Thus, in the ultrasonic diagnostic apparatus 11 according to the first embodiment, accurate blood flow velocity can be assessed regardless of the occurrence of aliasing.

In the ultrasonic diagnostic apparatus 11 according to the first embodiment, the residual image processing unit 115 uses the blood flow velocity data of the most recent frame and the blood flow velocity data of the immediately preceding frame to determine whether or not aliasing has occurred. As a configuration for performing such processing, the residual image processing unit 115 includes a frame memory unit (first memory unit) 104, an aliasing determination unit 105, a persistence coefficient determination unit 106, a persistence coefficient reference memory unit (third memory unit) 107, a persistence calculation unit 108, and a persistence memory unit (second memory unit) 109.

The frame memory unit 104 stores the CFM frame data of the most recent (currently being scanned) frame. The persistence memory unit 109 stores the CFM frame data and aliasing determination result outputted by the persistence calculation unit 108 for the frame immediately preceding the most recent frame. The CFM frame data stored in the persistence memory unit 109 is subjected to the persistence calculation, that is, residual image processing. In the following, blood flow velocity data of the CFM frame data stored in the frame memory unit 104 will be referred to as $V_{current}$, blood flow velocity data of CFM frame data stored in the persistence memory unit 109 will be referred to as $V_{out-1}$, and the aliasing determination result stored in the persistence memory unit 109 for the frame before the most recent frame will be referred to as $R_{aliasing-1}$.

The aliasing determination unit 105 performs aliasing determination on both the blood flow velocity data of CFM frame data from the frame memory unit 104, $V_{current}$, and the blood flow velocity data of CFM frame data from the persistence memory unit 109, $V_{out-1}$. More specifically, the aliasing determination unit 105 compares the blood flow velocity data $V_{current}$ and blood flow velocity data $V_{out-1}$ with a plurality of threshold values respectively, so as to determine whether or not aliasing has occurred in the blood flow velocity data for the most recent frame $V_{current}$ and the blood flow velocity data for the frame immediately preceding the most recent frame $V_{out-1}$, and outputs the determination results to the persistence coefficient determination unit 106 and the persistence calculation unit 108.

The persistence coefficient determination unit 106, based on the two determination results from the aliasing determination unit 105 (the determination results of $V_{current}$ and $V_{out-1}$) and the blood flow velocity data $V_{current}$ read from the frame memory unit 104, creates a reference index to the persistence coefficient reference memory unit 107. The persistence coefficient determination unit 106 accesses the persistence coefficient reference memory unit 107, reads the persistence coefficients mapped to the reference index, and sets them in the persistence calculation unit 108. In the persistence coefficient reference memory unit 107, a reference table of persistence coefficients corresponding to the values of blood flow velocity is stored in advance. The reference table includes two or more different persistence coefficients mapped according to the values of blood flow velocity.

The persistence calculation unit 108 performs the persistence calculation on the most recent blood flow velocity data $V_{current}$ based on the persistence coefficient set by the persistence coefficient determination unit 106 and two determination results from the aliasing determination unit 105. The persistence calculation is an operation that yields a residual image by performing a weighted addition on images of the current and of a plurality of consecutive frames and displaying the results.

Details regarding the processing performed by the aliasing determination unit 105, the persistence coefficient determination unit 106, and the persistence calculation unit 108 in the residual image processing unit 115 will be described later.

The CFM DSC unit 110 converts the coordinates of the blood flow velocity data output from the persistence calculation unit 108 and outputs it to the image combining unit 113.

The tomographic image signal processing unit 111 performs dynamic filtering on the received signal to remove unnecessary noise and then performs envelope detection processing and dynamic range compression processing, and outputs tomographic image frame data to the tomographic image DSC unit 112. The tomographic image DSC unit 112 converts the coordinates of the tomographic image frame data from the tomographic image signal processing unit 111, and outputs it to the image combining unit 113.

The image combining unit 113 combines frame data outputted from the CFM DSC unit 110 and the tomographic image DSC unit 112 in a way such that the frame data are combined for each pixel or for each corresponding measurement point to generate combined image frame data. Specifically, when blood flow velocity is zero, tomographic image frame data is displayed. Otherwise, two pieces of data for each pixel or data for each corresponding measurement point are combined such that the CFM frame data is displayed. It converts the data into color information according to the velocity and direction of blood flow and outputs it to the display 114. The display 114 displays data received from the image combining unit 113.

Processing of the Aliasing Determination Unit

Next, the aliasing determination method in the aliasing determination unit 105 and the determination method of the persistence coefficient in the persistence coefficient determination unit 106 will be described in more detail.

The aliasing determination unit 105 performs aliasing determination on the blood flow velocity data of the most recent CFM frame data $V_{current}$, which is read from the frame memory unit 104, and the residual image processed blood flow velocity data of CFM frame data for the frame immediately preceding the most recent frame $V_{out-1}$, which is read from the persistence memory unit 109. The aliasing determination unit 105 uses the read values of $V_{current}$ and $V_{out-1}$, and determines whether aliasing has occurred in $V_{current}$ or $V_{out-1}$.

FIG. 2 is a schematic diagram showing the velocity and direction of blood flow obtained based on the Doppler effect. FIG. 2 is a diagram showing a complex plane. Blood flow velocity can be expressed as a vector having a phase angle on the complex plane. That is, blood flow velocity increasing or decreasing corresponds to a vector on the complex plane, shown in FIG. 2, rotating around the origin.

Vectors $V_{current}$ and $V_{out-1}$ shown in FIG. 2 are the blood flow velocity data $V_{current}$ and $V_{out-1}$, of a certain frame, being generated by the CFM signal processing unit 103 and included in the CFM frame data, which are represented on a complex plane. As described above, in the complex plane shown in FIG. 2, the magnitude of the blood flow velocity data $V_{current}$ and $V_{out-1}$ corresponds to the rotation angle from the +X-axis (i.e., phase angle).

In the complex plane shown in FIG. 2, when the blood flow velocity is a positive value, the vector corresponding to the blood flow velocity is located in the first or second quadrant, and when the blood flow velocity is a negative value, the vector corresponding to the blood flow velocity is located in the third or fourth quadrant. Blood flow velocity with a positive value means that the blood flow is moving in a direction approaching the probe 101, whereas blood flow velocity with a negative value means that the blood flow is moving in a direction away from the probe 101.

In the complex plane, when the magnitude of the velocity vector corresponding to a certain blood flow velocity gradually increases from 0, the vector corresponding to the blood flow velocity data moves in the direction in which the rotation angle from the +X axis increases. Specifically, it moves in order from the first quadrant to the second quadrant, in the direction from the +X axis to the −X axis. When the blood flow velocity exceeds a predetermined value +$V_{max}$ or −$V_{max}$ (velocity corresponding to the frequency variation corresponding to ±PRF/2), crosses the −X axis and moves from the second quadrant to the third quadrant, aliasing occurs. In this case, the blood flow velocity, which should be a positive value, is measured as a negative value. When the magnitude of the velocity vector gradually decreases from 0, the vector corresponding to the blood flow velocity data moves in the direction opposite to the above.

Based on the above, the aliasing determination unit 105 determines whether or not aliasing has occurred in $V_{current}$ and $V_{out-1}$ by comparing the magnitude of the blood flow velocity data $V_{current}$ of the most recent frame as described below and the magnitude of the blood flow velocity data $V_{out-1}$ of the frame immediately preceding the most recent frame to a predetermined threshold Vth.

Here, as a method of aliasing determination, the method disclosed in Japanese Patent No. 5652395, the aliasing determination method adopted by the present invention will be described after the items that need to be improved (items that need improvement) in the method have been cited.

Existing Aliasing Determination Method (Method Disclosed in Japanese Patent No. 5652395)

Table 1 below shows the aliasing determination results obtained by using the existing aliasing method. In Table 1, the threshold value $V_{th}$ is the maximum value of the change in blood flow velocity assumed in the time interval between adjacent frames.

TABLE 1

| | Conditions | Aliasing |
|---|---|---|
| (0) | $V_{out-1} > 0$ and $V_{current} < -V_{th}$ | Confirmed |
| (1) | $V_{out-1} < 0$ and $V_{current} > V_{th}$ | Confirmed |
| (2) | $V_{out-1} < -V_{th}$ and $V_{current} > 0$ | Confirmed |
| (3) | $V_{out-1} > V_{th}$ and $V_{current} < 0$ | Confirmed |
| (4) | Other than (0) to (3) | Not confirmed |

As shown in condition (0) of Table 1, when the blood flow velocity data of the frame immediately preceding the most recent frame $V_{out-1}$ is positive and the blood flow velocity data of the most recent frame $V_{current}$ is smaller than $-V_{th}$, assuming that aliasing has not occurred, it is unnatural if the blood flow that was in the positive direction (direction approaching the probe 101) in the frame immediately preceding the most recent frame suddenly changes to high-velocity blood flow in the reversed negative direction (direction away from the probe 101). That is, it is presumed that the velocity of blood flow that was positive in the frame immediately preceding the most recent frame increases in the most recent frame, and the blood flow velocity corresponds to +PRF/2, that is, a value greater than the blood flow velocity in which aliasing has occurred. Therefore, when condition (0) is satisfied, aliasing is determined to have occurred in $V_{current}$. Condition (1) is a case where the sign of condition (0) is reversed. In the following, the blood flow velocity at which aliasing occurs is specified as $V_{max}$ or $-V_{max}$.

As shown in condition (2), when $V_{out-1}$ is smaller than $-V_{th}$, and $V_{current}$ becomes a positive value, assuming that aliasing has not occurred, it is unnatural if the high-velocity blood flow that was in the negative direction in the frame immediately preceding the most recent frame suddenly changes to blood flow in the reversed positive direction in the most recent frame. That is, it is presumed that with aliasing having occurred in $V_{out-1}$ and having a value larger than the +PRF/2, the blood flow velocity has slowed down in the most recent frame in the same positive direction. Accordingly, it is determined that aliasing has occurred. Condition (3) is a case where the sign of condition (2) is reversed.

If none of conditions (0) to (3) are satisfied, it is determined that aliasing has not occurred.

Items That Need Improvement in Existing Aliasing Determination Method

However, in the existing aliasing determination method described above, there are improvements that need to be made as described below. The first item that needs improvement is that, even if aliasing is determined to have occurred, it is not specified which of $V_{current}$ or $V_{out-1}$ aliasing has occurred in.

Specifically, for example, when $V_{out-1} > V_{th}$ and $V_{current} < -V_{th}$, thereby fulfilling condition (0) or condition (3) in Table 1 and aliasing is determined to have occurred, it may not be possible to specify which of $V_{current}$ or $V_{out-1}$ aliasing occurred in. That is, if condition (0) is true, aliasing has occurred in V current, and if condition (3) is true, aliasing has occurred in $V_{out-1}$. In such a case, it is not possible to specify which one aliasing occurred in. Also, even when $V_{out-1} < -V_{th}$ and $V_{current} < V_{th}$, corresponding to condition (1) or condition (2), there may be instances where it is not possible to specify which one is aliasing in a similar manner.

The second item that needs improvement is that, in some cases, aliasing is determined not to have occurred even though aliasing has actually occurred. Specifically, for example, when $V_{out-1} < -V_{th}$ and $V_{current} < -V_{th}$, thereby fulfilling condition (4) in Table 1, aliasing is determined not to have occurred, and in fact, the, even when aliasing is determined to have occurred in both $V_{current}$ and $V_{out-1}$, $V_{out-1} < -V_{th}$ and $V_{current} < -V_{th}$ can be satisfied. It is the same when $V_{out-1} > V_{th}$ and $V_{current} > V_{th}$.

The aliasing determination method of the present invention to be described below is to improve on such existing aliasing determination methods.

Aliasing Determination Method of the Aliasing Determination Unit of the Present Invention In the present invention, the aliasing determination unit 105 performs aliasing determination based on the magnitude of blood flow velocity data of the most recent frame $V_{current}$, the magnitude of blood flow velocity data of the frame immediately preceding the most recent frame $V_{out-1}$, and the aliasing determination result $R_{aliasing-1}$ of the frame immediately preceding the most recent frame. Table 2 below shows aliasing determination results from the aliasing determination unit 105. In Table 2, "aliasing present" means the aliasing determination result of the frame immediately preceding the most recent frame $R_{aliasing-1}$ determined that aliasing has occurred, and "aliasing absent" means the aliasing determination result of the frame immediately preceding the most recent frame $R_{aliasing-1}$ determined that aliasing has not occurred.

TABLE 2

| | Conditions | Aliasing in $V_{current}$ | Aliasing in $V_{out-1}$ |
|---|---|---|---|
| (10) | $V_{out-1} < -V_{th}$ and $V_{current} < -V_{th}$ and Aliasing confirmed | Confirmed | Confirmed |
| (11) | $V_{out-1} > V_{th}$ and $V_{current} > V_{th}$ and Aliasing confirmed | Confirmed | Confirmed |
| (12) | $V_{out-1} > 0$ and $V_{current} < -V_{th}$ and Aliasing not confirmed | Confirmed | Not confirmed |
| (13) | $V_{out-1} < 0$ and $V_{current} >$ Vth and Aliasing not confirmed | Confirmed | Not confirmed |
| (14) | $V_{out-1} < -V_{th}$ and $V_{current} > 0$ and Aliasingconfirmed | Not confirmed | Confirmed |
| (15) | $V_{out-1} > V_{th}$ and $V_{current} < 0$ and Aliasing confirmed | Not confirmed | Confirmed |
| (16) | Other than (10) to (15) | Not confirmed | Not confirmed |

As shown in condition (10) of Table 2, in the case where $V_{out-1} < -V_{th}$ and $V_{current} < -V_{th}$, as described above, in practice, either aliasing has occurred in both $V_{current}$ and $V_{out-1}$, or aliasing has occurred in neither. Therefore, the aliasing determination unit 105 refers to $R_{aliasing-1}$ and when the aliasing determination result for the frame immediately preceding the most recent frame $R_{aliasing-1}$ is "aliasing present" as shown in condition (10), it determines that aliasing has also occurred in $V_{current}$ and $V_{out-1}$. The reason for this is as follows. Since the aliasing determination result $R_{aliasing-1}$ for the frame immediately preceding the most recent frame being "aliasing present" means that aliasing has occurred in $V_{out-1}$, $V_{out-1}$ is larger than +PRF/2. In this case, supposing that aliasing has not occurred in $V_{current}$, it is unnatural if the extremely high-velocity blood flow with a velocity that exceeds +PRF/2 in the positive direction in the frame immediately preceding the most recent frame suddenly changes to a high-velocity blood flow in the reversed negative direction in the most recent frame. For this reason, even in the most recent frame, it is estimated to be an extremely high-velocity flow that exceeds a value corresponding to that of the positive directional +PRF/2. Shown in condition (11), it is the same when $V_{out-1} < -V_{th}$ and $V_{current} < -V_{th}$.

Figure 3A:
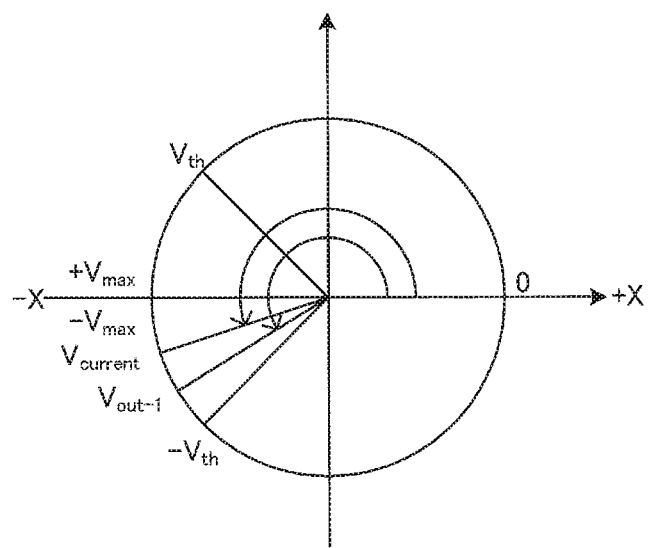
FIG. 3A shows a complex plane $V_{current}$ and $V_{out-1}$ of condition (10)
Figure 3B:
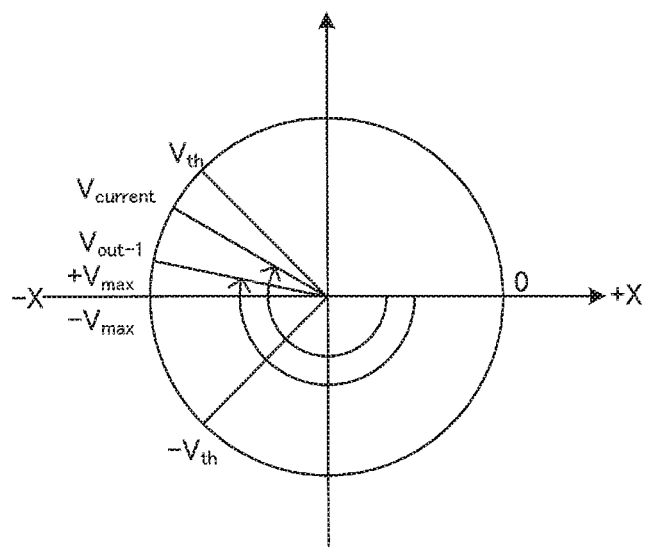
FIG. 3B shows a complex plane $V_{current}$ and $V_{out-1}$ of condition (11)

FIG. 3A is a diagram showing $V_{current}$ and $V_{out-1}$ of condition (10) on the same complex plane shown in FIG. 2. FIG. 3B is a diagram showing $V_{current}$ and $V_{out-1}$ of condition (11) on the same complex plane shown in FIG. 2.

As shown in condition (12), in the case where $V_{out-1} > 0$ and $V_{current} < -V_{th}$, and the aliasing determination result $R_{aliasing-1}$ is "aliasing absent" because aliasing has not occurred in $V_{out-1}$, for the same reason as in condition (0) of Table 1, the aliasing determination unit 105 determines that aliasing has not occurred in $V_{out-1}$ and has occurred in $V_{current}$. Condition (13) is a case where the sign of condition (12) is reversed.

Figure 3C:
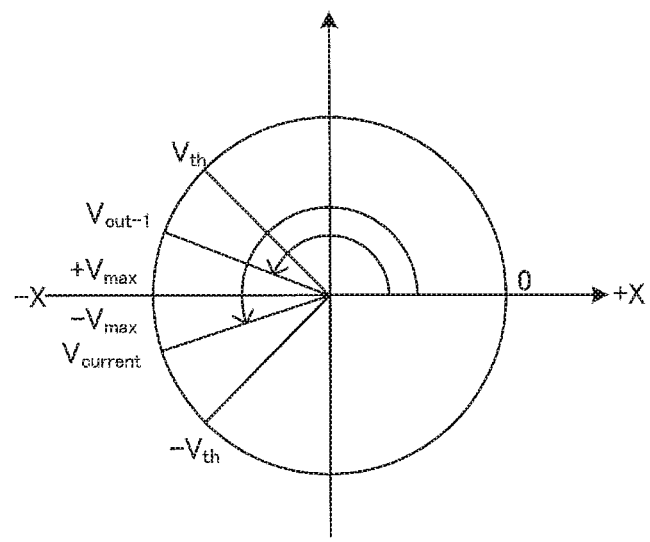
FIG. 3C shows a complex plane $V_{current}$ and $V_{out-1}$ of condition (12)
Figure 3D:
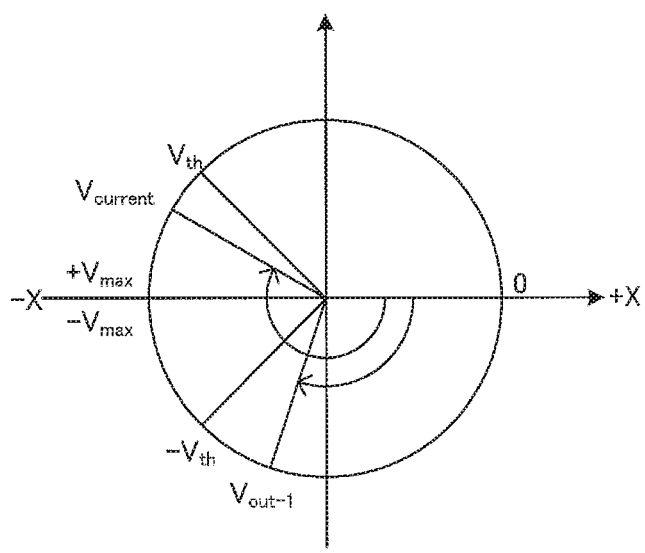
FIG. 3D shows a complex plane $V_{current}$ and $V_{out-1}$ of condition (13)

FIG. 3C is a diagram showing $V_{current}$ and $V_{out-1}$ of condition (12) on the same complex plane shown in FIG. 2. FIG. 3D is a diagram showing $V_{current}$ and $V_{out-1}$ of condition (13) on the same complex plane shown in FIG. 2.

As shown in condition (14), in the case where $V_{out-1}$ is smaller than $-V_{th}$, $V_{current}$ becomes positive, and in the case where the aliasing determination result $R_{aliasing-1}$ is "aliasing present", aliasing has occurred in $V_{out-1}$. In this case, for the same reason as in condition (2) of Table 1, the aliasing determination unit 105 determines that aliasing has occurred in $V_{out-1}$ and has not occurred in $V_{current}$. Condition (15) is a case where the sign of condition (14) is reversed.

Figure 3E:
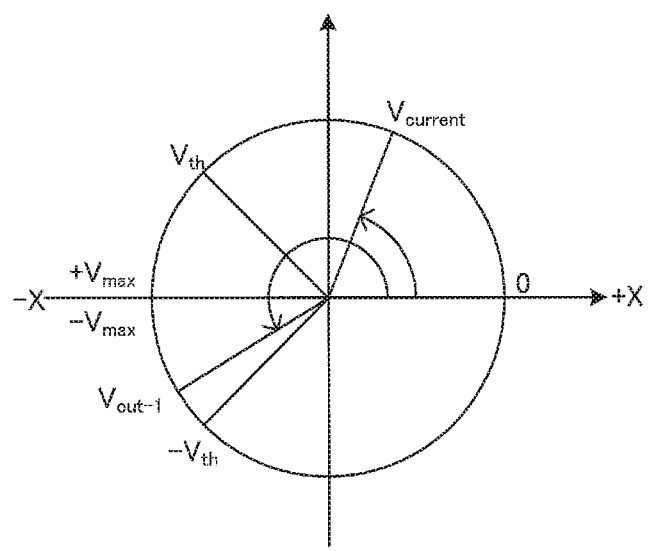
FIG. 3E shows a complex plane $V_{current}$ and $V_{out-1}$ of condition (14)
Figure 3F:
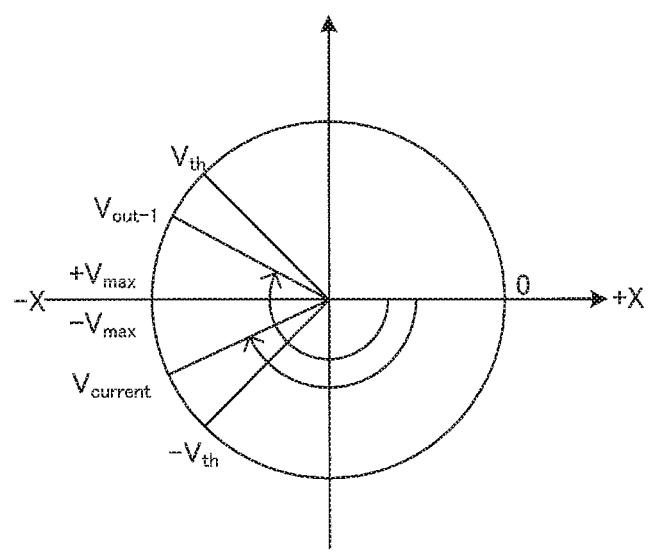
FIG. 3F shows a complex plane $V_{current}$ and $V_{out-1}$ of condition (15)

FIG. 3E is a diagram showing $V_{current}$ and $V_{out-1}$ of condition (14) on the same complex plane shown in FIG. 2. FIG. 3F is a diagram showing $V_{current}$ and $V_{out-1}$ of condition (15) on the same complex plane shown in FIG. 2.

Here, since, in the case where $V_{out-1} > V_{th}$ and $V_{current} < -V_{th}$, if the aliasing determination result $R_{aliasing-1}$ is "aliasing absent", condition (12) is fulfilled, and if the aliasing determination result $R_{aliasing-1}$ is "aliasing present", condition (15) is fulfilled, the presence or absence of aliasing can be determined for each value of $V_{current}$ and $V_{out-1}$. Also, even when $V_{out-1} < -V_{th}$ and $V_{current} > V_{th}$, similarly fulfilling condition (13) or condition (14), the presence or absence of aliasing in $V_{current}$ and $V_{out-1}$ can be specified.

If none of conditions (10) to (15) are satisfied, the aliasing determination unit 105 determines that aliasing has not occurred (condition (16)).

Thus, even if whether or not aliasing has occurred can not be accurately determined with the existing aliasing determination method, it is possible to accurately determine whether or not aliasing has occurred with the aliasing determination method of the aliasing determination unit 105 of the present invention.

Processing by the Persistence Coefficient Determination Unit

Next, the method by which the persistence coefficient determination unit 106 sets persistence numbers to the persistence calculation unit 108 will be described.

The persistence coefficient determination unit 106 creates a reference index for the persistence coefficient reference memory unit 107 based on the aliasing determination results, outputted from the aliasing determination unit 105, of the blood flow velocity data $V_{current}$ for the most recent frame and blood flow velocity data $V_{out-1}$ for the frame immediately preceding the most recent frame, and the absolute value of $V_{current}$ read from the frame memory unit 104. Table 3 below shows the reference index created by the persistence coefficient determination unit 106.

TABLE 3

| Condition | Aliasing in $V_{current}$ | Aliasing in $V_{out-1}$ | Reference Indexes (Idx) |
|---|---|---|---|
| (10) | Confirmed | Confirmed | $V_{max}$ |
| (11) | Confirmed | Confirmed | $V_{max}$ |
| (12) | Confirmed | Not confirmed | $V_{max}$ |
| (13) | Confirmed | Not confirmed | $V_{max}$ |
| (14) | Not confirmed | Confirmed | Abs ($V_{current}$) |
| (15) | Not confirmed | Confirmed | Abs ($V_{current}$) |
| (16) | Not confirmed | Not confirmed | Abs ($V_{current}$) |

When aliasing has occurred in $V_{current}$, it is possible that the blood flow velocity $V_{current}$ has a magnitude such that it exceeds the absolute value of $V_{max}$ or $-V_{max}$. For this reason, the reference index becomes $V_{max}$. Otherwise, it becomes the absolute value of $V_{current}$, Abs($V_{current}$).

In the persistence coefficient reference memory unit 107, a reference table composed of persistence coefficients mapped to the reference index is stored. The persistence coefficient determination unit 106 accesses the persistence coefficient reference memory unit 107, reads the persistence coefficients mapped to the created reference index, and outputs them to the persistence calculation unit 108.

Figure 4:
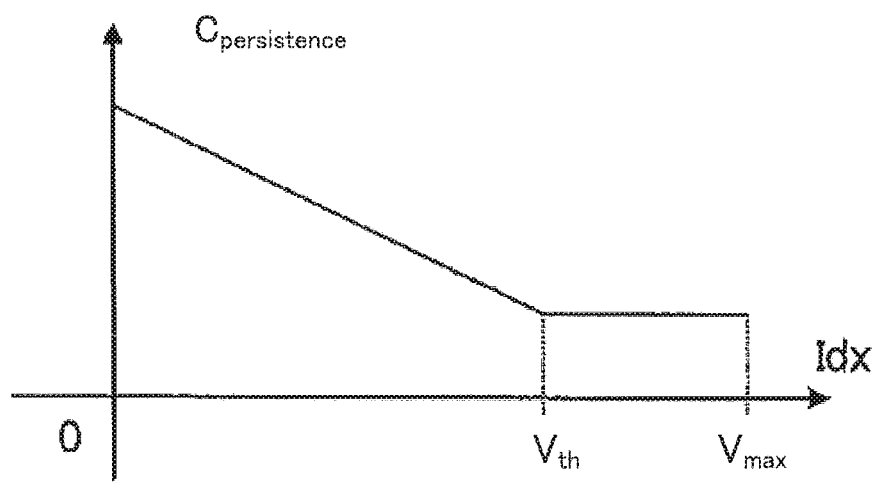
FIG. 4 is a graph showing an example of the relationship between the reference index and the persistence coefficient.

FIG. 4 is a graph showing an example of the relationship between the reference index and the persistence coefficient. In FIG. 4, the horizontal axis represents the reference index, and the vertical axis shows the persistence coefficient. As shown in Table 3, the reference index is $V_{max}$ or the absolute value of $V_{current}$, Abs($V_{current}$). When the absolute value of $V_{current}$ is lower than the threshold $V_{th}$, the persistence coefficient $C_{persistence}$, which decreases steadily with increasing $V_{current}$, is mapped to $V_{current}$. That is, when the absolute value of $V_{current}$ is lower than the threshold $V_{th}$, a persistence coefficient $C_{persistence}$, which is proportional and different from the blood flow velocity of the most recent frame $V_{current}$, is mapped to $V_{current}$.

As described above, the persistence calculation is a calculation that yields a residual image effect by performing weighted addition on images of the current and of a plurality of consecutive frames and utilizing the display of the results. Details regarding the persistence calculation will be described later.

Processing by the Persistence Calculation Unit 108

The persistence calculation unit 108 performs the persistence calculation on the most recent blood flow velocity data $V_{current}$ based on the persistence coefficient set by the persistence coefficient determination unit 106 and two determination results obtained from the aliasing determination unit 105.

When the determination result from the aliasing determination unit 105 for $V_{current}$ is true, i.e., when aliasing is determined to have occurred in $V_{current}$, the persistence calculation unit 108, before performing the persistence calculation, performs the following correction to $V_{current}$. Specifically, when $V_{current}<0$, the persistence calculation unit 108 corrects $V_{current}$ by adding the repetition frequency PRF to $V_{current}$ ($V_{current}$+PRF), and when $V_{current}>0$, $V_{current}$ is corrected by subtracting PRF from $V_{current}$ ($V_{current}$−PRF).

Similarly, when the determination result from the aliasing determination unit 105 for $V_{out-1}$ is true, i.e., when aliasing is determined to have occurred in $V_{out-1}$, the persistence calculation unit 108, before performing the persistence calculation, performs a correction to $V_{out-1}$ similar to that described above for $V_{current}$. Specifically, when $V_{out-1}<0$, the persistence calculation unit 108 corrects $V_{out-1}$ to $V_{out-1}$+ PRF. When $V_{out-1}>0$, the persistence calculation unit 108 corrects $V_{out-1}$ to $V_{out-1}$+PRF.

The persistence calculation unit 108, using the blood flow velocity data $V_{current}$ and $V_{out-1}$, performs the persistence calculation with the following equation (1).

$$V_{out}=(1-C_{persistence})\times V_{current}+C_{persistence}\times V_{out-1}. \quad (1)$$

In equation (1), $V_{out}$ is the blood flow velocity data that was subjected to the persistence calculation (residual image processing) in the most recent frame, and $C_{persistence}$ is the persistence coefficient ($0 \le C$ persistence$\le 1$) set by the persistence coefficient determination unit 106.

When upon performing the persistence calculation using equation (1) as described above, $V_{out}>+PRF/2$, the persistence calculation unit 108 corrects $V_{out}$ to $V_{out}$−PRF, and when $V_{out}$ is $<-PRF/2$, $V_{out}$ is corrected to $V_{out}$+PRF. The persistence calculation unit 108 outputs the corrected $V_{out}$ to the CFM DSC unit 110 and the persistence memory unit 109.

By such processing, even if aliasing has occurred in $V_{current}$, $V_{out-1}$ or $V_{out}$, $V_{out}$ that has the effect of aliasing canceled can be calculated.

The persistence calculation by the persistence calculation unit 108 described above is performed for each pixel or each measurement point of one frame of blood flow velocity data (CFM frame data).

Thus, by using a persistence coefficient set by the persistence coefficient determination unit 106, the persistence calculation unit 108 can obtain the following results by performing the persistence calculation.

That is, in the case where the magnitude of blood flow velocity $V_{current}$ of the most recent frame is small, because the persistence coefficient $C_{persistence}$ set by the persistence coefficient determination unit 106 increases, the weight of the blood flow velocity $V_{out-1}$ of the immediately preceding frame increases when the persistence calculation unit 108 performs the persistence calculation such as in equation (1). As a result, when $V_{current}$ when is small, $V_{out}$, that strongly reflects $V_{out-1}$ and is the persistence calculation result of the persistence calculation, is calculated. Because of this, using $V_{out}$, the change in the color flow mapping image generated by the CFM DSC unit 110 and the image combining unit 113 becomes smooth and black spots are less likely to occur.

Also, in the case where $V_{current}$ is large, because the persistence coefficient $C_{persistence}$ set by the persistence coefficient determination unit 106 decreases, the weight of $V_{out-1}$ decreases when the persistence calculation unit 108 performs the persistence calculation such as in equation (1). As a result, in the case where $V_{current}$ is large, with the influence of $V_{out-1}$ being small, $V_{out}$ is calculated, and it is possible to realize a color flow mapping image reflecting the sharp increase in blood flow velocity in real time.

Moreover, the persistence coefficient determination unit 106 monotonically reduces the persistence coefficient $C_{persistence}$ with increases in persistence. Therefore, in the case where the blood flow velocity increases with time, the persistence coefficient determination unit 106 decreases the persistence coefficient $C_{persistence}$ with time, so the residual image effect from the persistence calculation of the persistence calculation unit 108 decreases and the color flow mapping image changes abruptly. Conversely, in the case where the blood flow velocity decreases with time, the persistence coefficient determination unit 106 increases the persistence coefficient $C_{persistence}$ with time, so the residual image effect from the persistence calculation of the persistence calculation unit 108 increases and the color flow mapping image changes slowly.

Back to the description of the processing of persistence calculation unit 108. The persistence calculation unit 108, using the persistence calculation result $V_{out}$, determines whether or not aliasing has occurred in the last frame in blood flow velocity data $V_{out}$ that had been subjected to residual image processing after performing the persistence calculation using equation (1). Here, the persistence calculation unit 108 determines that aliasing has occurred in $V_{out}$ when $V_{out}>+PRF/2$ or $V_{out}<-PRF/2$; otherwise (−PRF/$2 \le V_{out} \le PRF/2$), it determines that aliasing has not occurred.

The persistence calculation unit 108 then outputs the aliasing determination result $R_{aliasing}$ of the blood flow velocity data $V_{out}$ of the most recent frame to the persistence memory unit 109. The aliasing determination result $R_{aliasing}$ that is outputted from the persistence calculation unit 108 is stored in the persistence memory unit 109, and at the time of processing in the next frame, the aliasing determination result $R_{aliasing-1}$ of the frame immediately preceding the most recent frame is outputted to the aliasing determination unit 105.

Operation and Results

As described above, in the ultrasonic diagnostic apparatus 11 according to the first embodiment of the present invention, the aliasing determination unit 105 adds the blood flow velocity $V_{current}$ of the most recent frame and the blood flow velocity $V_{out-1}$ of the frame preceding the most recent frame, and based on the aliasing determination result $R_{aliasing-1}$ of the blood flow velocity data that was determined for the frame preceding the most recent frame, with the frame having been subjected to residual image processing, performs the aliasing determination. Because of this, whether or not aliasing has occurred in the blood flow velocity data $V_{current}$ of the most recent frame and the blood flow velocity data $V_{out-1}$ of the frame immediately preceding the most recent frame can be accurately determined.

Further, in the ultrasonic diagnostic apparatus 11 according to the first embodiment of the present invention, based on the result of the aliasing determination of such an aliasing determination method, the persistence calculation unit 108 is performs the persistence calculation using $V_{current}$ and $V_{out-1}$ and outputs the result. Therefore, it is possible to generate and display a tomographic image that accurately reflects blood flow velocity.

Furthermore, in the ultrasonic diagnostic apparatus 11 according to the first embodiment of the present invention, based on the blood flow velocity data $V_{out}$ of the most recent frame and has been subjected to residual image processing, which is the result from the persistence calculation, the persistence calculation unit 108 determines whether or not aliasing has occurred in $V_{out}$ and outputs that result $R_{aliasing}$ to the persistence memory unit 109. Then, in the processing of the next frame, the persistence memory unit 109 outputs $V_{out}$ inputted in the processing of the previous frame as $V_{out\text{-}1}$ of the next frame, and outputs $R_{aliasing}$ inputted in the processing of the previous frame as $R_{aliasing\text{-}1}$.

Then, in the ultrasonic diagnostic apparatus 11 according to a first embodiment of the present invention, when aliasing is determined to have occurred in the blood flow velocity data $V_{current}$ for the most recent frame or the blood flow velocity data $V_{out\text{-}1}$ for the frame immediately preceding the most recent frame, the persistence calculation unit 108 performs corrections on the blood flow velocity data in which aliasing occurred. Furthermore, the persistence calculation unit 108 determines whether or not aliasing has occurred for the most recent frame in the blood flow velocity data $V_{out}$ that has been subjected to residual image processing, and performs a correction to $V_{out}$ when aliasing is determined to have occurred. Therefore, even if aliasing has occurred in $V_{current}$, $V_{out\text{-}1}$ or $V_{out}$, $V_{out}$ that has the effect of aliasing canceled can be calculated.

Second Embodiment

Figure 5:
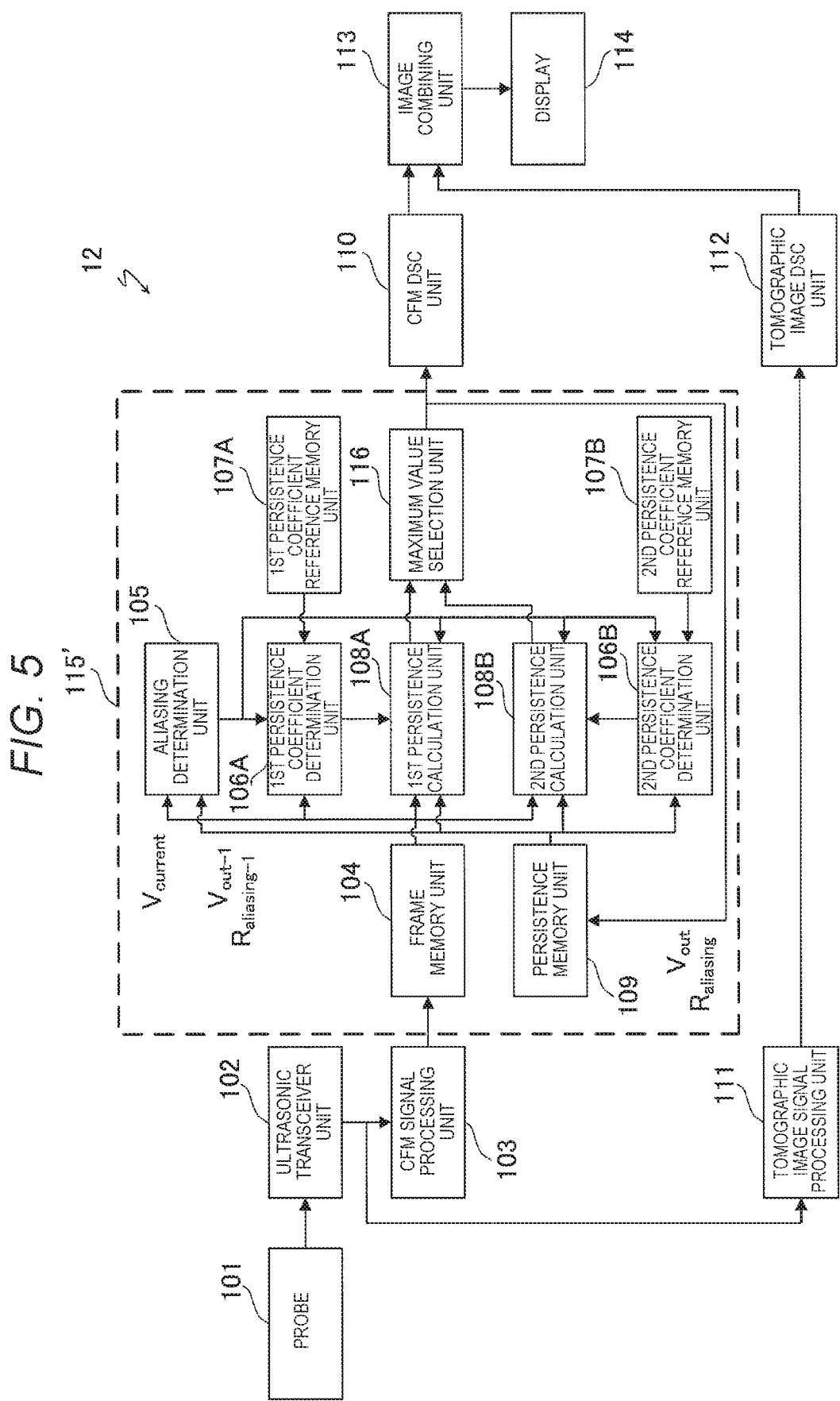
FIG. 5 is a block diagram showing an example configuration of an ultrasonic diagnostic apparatus according to the second embodiment of the present invention.

The following describes the ultrasonic diagnostic apparatus 12 according to the second embodiment of the present invention. FIG. 5 is a block diagram showing an example configuration of an ultrasonic diagnostic apparatus according to the second embodiment of the present invention.

The ultrasonic diagnostic apparatus 12 shown in FIG. 5 is different from the first embodiment of the ultrasonic diagnostic apparatus 11 described above in that the residual image processing unit has two persistence coefficient determination units, two persistence coefficient reference memory units and two persistence calculation units. In the following, a description will be given only for the differences from the first embodiment.

As shown in FIG. 5, the residual image processing unit 115' includes a frame memory unit 104, an aliasing determination unit 105, a first persistence coefficient determination unit 106A, a second persistence coefficient determination unit 106B, a first persistence coefficient reference memory unit 107A, a second persistence coefficient reference memory unit 107B, a first persistence calculation unit 108A, a second persistence calculation unit 108B, and a persistence memory unit 109.

The first persistence coefficient determination unit 106A creates the first reference index for the first persistence coefficient reference memory unit 107A based on the two aliasing determination results outputted from the aliasing determination unit 105 and the absolute value of $V_{current}$ read from the frame memory unit 104. Information regarding the first reference index will be described later.

The first persistence coefficient determination unit 106A accesses the first persistence coefficient reference memory unit 107A, reads out the first persistence coefficient mapped to the first reference index, and sets them to the first persistence calculation unit 108A. In the first persistence coefficient reference memory unit 107A, a first reference table containing first persistence coefficients mapped to the magnitude of blood flow velocity data is stored in advance. The first reference table includes two or more different persistence coefficients that are mapped to the magnitude of blood flow velocity data.

In contrast, the second persistence coefficient determination unit 106B creates a second reference index for the second persistence coefficient reference memory unit 107B based on the two aliasing determination results outputted from the aliasing determination unit 105 and the absolute value of $V_{out\text{-}1}$ read from the persistence memory unit 109. Creation of the second reference index in the second persistence coefficient determination unit 106B will be described later.

The second persistence coefficient determination unit 106B accesses the second persistence coefficient reference memory unit 107B, reads the second persistence coefficients mapped to the second reference index, and sets them in the second persistence calculation unit 108B. The second persistence coefficient reference memory unit 107B, a second reference table containing second persistence coefficients mapped to the magnitude of blood flow velocity data is stored in advance. Although the second reference table also includes persistence coefficients of two or more different values that are mapped according to the values of blood flow velocity, as explained in detail below, the values are different from the first persistence coefficient and second persistence coefficient that are mapped to the same blood flow velocity value.

Similar to the persistence calculation unit 108 of the first embodiment, after correcting for aliasing, the first persistence calculation unit 108A performs the persistence calculation on $V_{current}$ and $V_{out\text{-}1}$ using equation (1) based on the persistence coefficient set by the first persistence coefficient determination unit 106A and the two determination results from the aliasing determination unit 105.

Similar to the persistence calculation unit 108 of the first embodiment, after correcting for aliasing, the second persistence calculation unit 108B performs the persistence calculation on $V_{current}$ and $V_{out\text{-}1}$ using equation (1) based on the persistence coefficient set by the second persistence coefficient determination unit 106B and the two determination results from the aliasing determination unit 105.

Calculations of the first persistence calculation unit 108A and second persistence calculation unit 108B are the same except for their differing set persistence coefficients.

The first persistence calculation unit 108A and the second persistence calculation unit 108B output their respective results for the persistence calculation to the maximum value selection unit 116.

Based on the persistence calculation results inputted from the first persistence calculation unit 108A and the second persistence calculation unit 108B, for each pixel or for each value of the corresponding measurement point, the maximum value selection unit 116 compares the absolute value of the blood flow velocity data which is the result of the persistence calculation, the larger value is selected, and blood flow velocity data $V_{out}$ subjected to residual image processing is generated for the most recent frame.

The maximum value selection unit 116 corrects $V_{out}$ for aliasing, as performed by the persistence calculation unit 108 of the first embodiment.

Then, the maximum value selection unit 116 outputs the corrected $V_{out}$ to the CFM DSC unit 110 and the persistence memory unit 109.

Furthermore, the maximum value selection unit 116, as performed by the persistence calculation unit 108 of the first embodiment, determines whether or not aliasing has occurred in the most recent frame in the blood flow velocity data $V_{out}$ that are subjected to residual image processing. The maximum value selection unit 116 then outputs the aliasing determination result $R_{aliasing}$ of the blood flow velocity data $V_{out}$ in the most recent frame to the persistence memory unit 109.

Next, a method of determining the first and second persistence coefficients will be described in detail. As described above, the first persistence coefficient determination unit 106A creates the first reference index for persistence coefficient reference memory unit 107A based on the two folded determination results outputted from the aliasing determination unit 105 and the absolute value of $V_{current}$ read from the frame memory unit 104.

The first reference index created in Table 4 is shown.

TABLE 4

| Condition | Aliasing in $V_{current}$ | Aliasing in $V_{out-1}$ | Reference Indexes in First Persistence Coefficient Determininion Unit (Idx1) | Reference Indexes in Second Persistence Coefficient Determininion Unit (Idx2) |
|---|---|---|---|---|
| (10) | Confirmed | Confirmed | $V_{max}$ | $V_{max}$ |
| (11) | Confirmed | Confirmed | $V_{max}$ | $V_{max}$ |
| (12) | Confirmed | Not confirmed | $V_{max}$ | Abs $(V_{out-1})$ |
| (13) | Confirmed | Not confirmed | $V_{max}$ | Abs $(V_{out-1})$ |
| (14) | Not confirmed | Confirmed | Abs $(V_{current})$ | $V_{max}$ |
| (15) | Not confirmed | Confirmed | Abs $(V_{current})$ | $V_{max}$ |
| (16) | Not confirmed | Not confirmed | Abs $(V_{current})$ | Abs $(V_{out-1})$ |

When aliasing has occurred in $V_{current}$, it is possible that $V_{current}$ exceeds the absolute value of $V_{max}$ or $-V_{max}$. Therefore, when aliasing has occurred in $V_{current}$, the first reference index becomes $V_{max}$. Otherwise, it becomes the absolute value of $V_{current}$, Abs($V_{current}$).

Figure 6A:
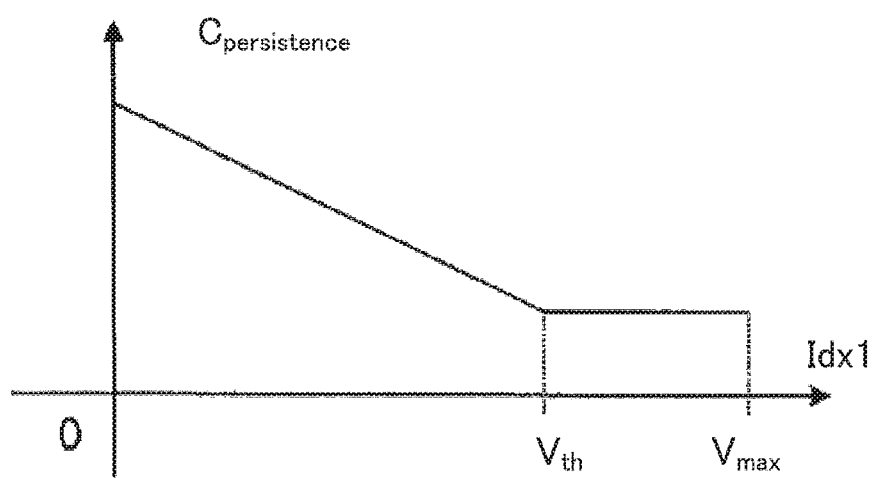
FIG. 6A is a graph showing an example of the relationship between the first reference index and the first persistence coefficient.

FIG. 6A is a graph showing an example of the relationship between the first reference index and the first persistence coefficient. In FIG. 6A, the horizontal axis represents the first reference index and the vertical axis shows the first persistence coefficient. As shown in Table 4, the first reference index is $V_{max}$ or the absolute value of $V_{current}$, Abs ($V_{current}$). When the absolute value of $V_{current}$ is lower than the threshold $V_{th}$, the first persistence coefficient $C_{persistence}$, which decreases steadily with increasing $V_{current}$, is mapped to $V_{current}$. That is, when the absolute value of $V_{current}$ is lower than the threshold $V_{th}$, a persistence coefficient $C_{persistence}$, which is proportional and different from the blood flow velocity of the most recent frame $V_{current}$, is mapped to $V_{current}$.

On the other hand, the second persistence coefficient determination unit 106B creates a second reference index for the persistence coefficient reference memory unit 107B based on the two aliasing determination results outputted by the aliasing determination unit 105 and the absolute value of $V_{out-1}$ outputted by the persistence memory unit 109. Refer to Table 4 for the second reference index.

When aliasing has occurred in $V_{out-1}$, it is possible that $V_{out-1}$ exceeds the absolute value of $V_{max}$ or $-V_{max}$. Therefore, when aliasing has occurred in $V_{out-1}$, the second reference index becomes $V_{max}$. Otherwise, it becomes the absolute value of $V_{out-1}$, Abs($V_{out-1}$).

Figure 6B:
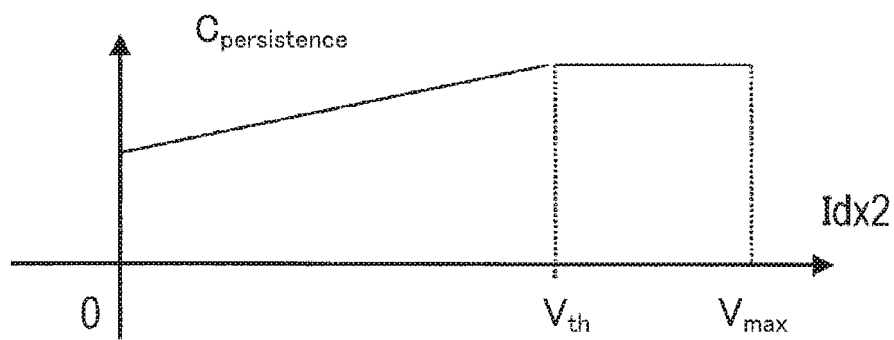
FIG. 6B is a graph showing an example of the correspondence relationship between the second reference index and the second persistence coefficient.

FIG. 6B is a graph showing an example of the correspondence relationship between the second reference index and the second persistence coefficient. In FIG. 6B, the horizontal axis represents the second reference index and the vertical axis shows the second persistence coefficient. As shown in Table 4, the second reference index is $V_{max}$ or the absolute value of $V_{out-1}$, Abs($V_{out-1}$). When the absolute value of $V_{out-1}$ is lower than the threshold $V_{th}$, the second persistence coefficient $C_{persistence}$, which decreases steadily with increasing $V_{current}$, is mapped to $V_{current}$. That is, when the absolute value of $V_{out-1}$ is lower than the threshold $V_{th}$, a persistence coefficient $C_{persistence}$, which is proportional and different from the blood flow velocity of the frame before the lastest frame $V_{out-1}$, is mapped to $V_{out-1}$.

As shown in FIGS. 6A and 6B, the first persistence coefficient is mapped to the blood flow velocity of the most recent frame $V_{current}$, and the value of the first persistence coefficient is as small as the magnitude of the absolute value of $V_{current}$. The greater the first persistence factor, since the operation more considering the blood flow velocity of the previous frame, the first persistence calculation unit 108A reduces residual image effect, quickly changing the blood flow velocity performing an operation to be. In contrast, the second persistence coefficient, blood flow velocity V of the previous frame$_{out-1}$ mapped to, and, $V_{out-1}$ for a larger value as the absolute value is large, the second persistence calculation unit 108B increases the residual image effect, reduce operation changes in blood flow velocity.

The first persistence calculation unit 108A as described above, to reduce the residual image effect, quickly for performing the operation of changing the blood flow velocity, monotonously the first persistence coefficient as the first reference index is increased reduced, it can realize a color flow mapping image reflecting the sharp increase in blood flow velocity in real time as the blood flow velocity becomes higher.

When the second persistence calculation unit 108B adds color to the color tone or gradation in the blood flow image as the blood flow velocity increases to display an image with an enhanced residual image effect, a dark display will be shown as a residual image for an unnecessarily long time when the blood flow velocity is low. For example, when the probe is moved, the blood flow looks as if it had a tail. Because of this, the second persistence coefficient is increased monotonically as the second reference index is increased, and it becomes possible to suppress the residual image effect as the blood flow velocity decreases.

Third Embodiment

Figure 7:
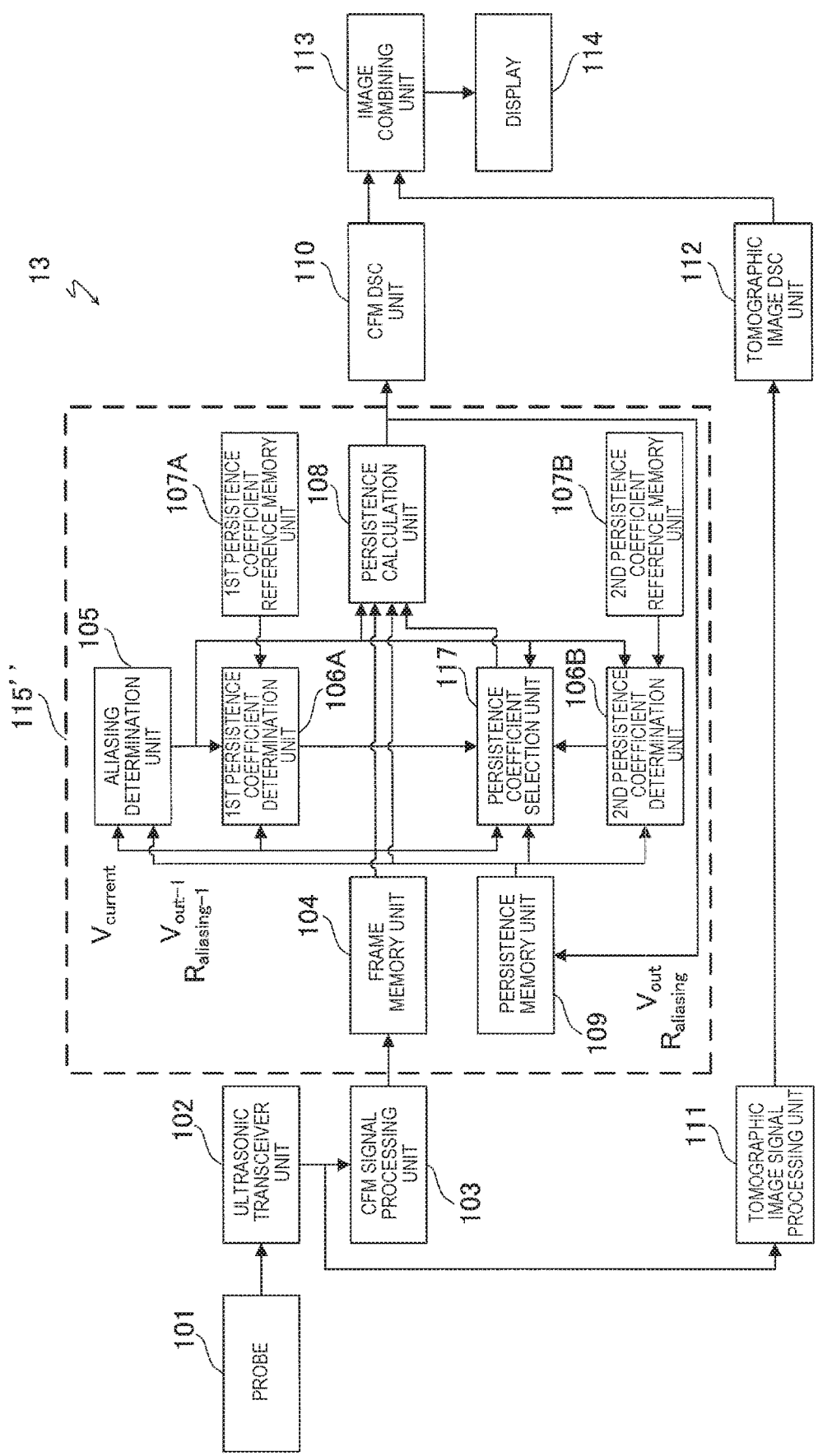
FIG. 7 is a block diagram showing an example configuration of an ultrasonic diagnostic apparatus according to the third embodiment of the present invention.
Figure 8:
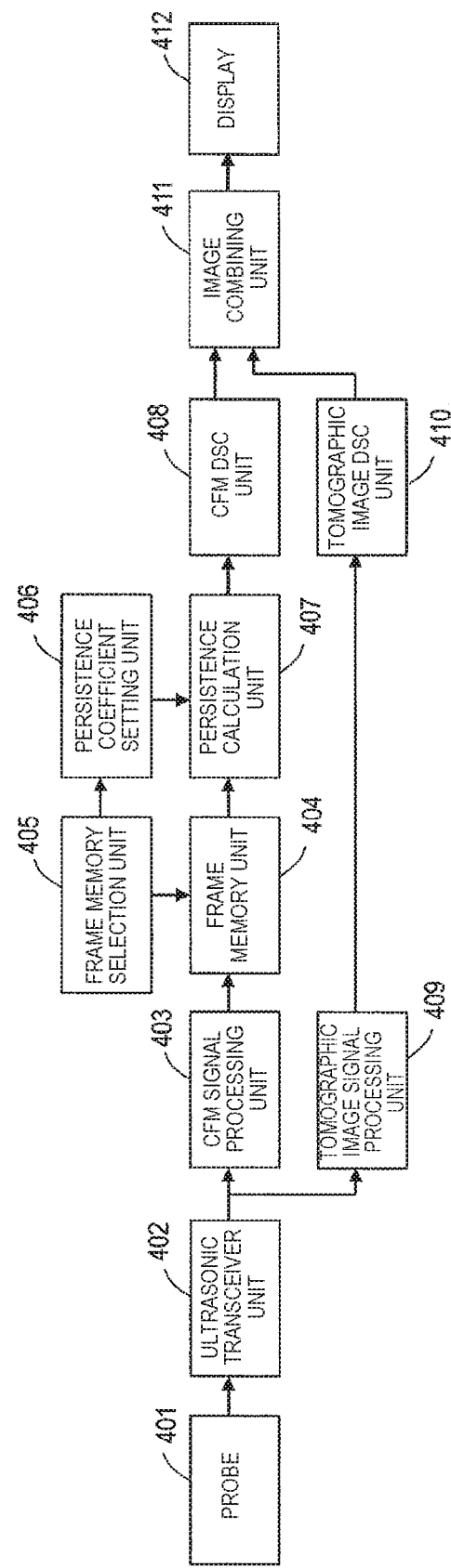
FIG. 8 is a block diagram showing an example configuration of an existing ultrasonic diagnostic apparatus.

The following describes the ultrasonic diagnostic apparatus 13 according to the third embodiment of the present invention. FIG. 7 is a block diagram showing an example configuration of an ultrasonic diagnostic apparatus according to the third embodiment of the present invention.

The ultrasonic diagnostic apparatus 13 shown in FIG. 7 is different from the first embodiment of the ultrasonic diagnostic apparatus 11 described above in that the residual image processing unit has two persistence coefficient determination units and two persistence coefficient reference memory units, and the two persistence coefficient determination units have a persistence coefficient selection unit that selects from the set persistence coefficients. In the following, a description will be given only of the differences from the first and second embodiments.

As shown in FIG. 7, the residual image processing unit 115" includes a frame memory unit 104, an aliasing determination unit 105, a first persistence coefficient determination unit 106A, a second persistence coefficient determination unit 106B, a persistence coefficient selection unit 117, a first persistence coefficient reference memory unit 107A, a second persistence coefficient reference memory unit 107B, a persistence calculation unit 108, and a persistence memory unit 109.

The persistence coefficient selection unit 117 reads the blood flow velocity data $V_{current}$ for the most recent frame from the frame memory unit 104 and the blood flow velocity data $V_{out-1}$ for the frame preceding the most recent frame from the persistence memory unit 109, compares the absolute values of $V_{current}$ and $V_{out-1}$, and based on the comparison results, selects one of either the first persistence coefficient set by the first persistence coefficient determination unit 106A or the second persistence coefficient set by the second persistence coefficient determination unit 106B to set in the persistence calculation unit 108.

Specifically, the persistence coefficient selection unit 117, in the case where the absolute value of $V_{current}$ is larger than the absolute value of $V_{out-1}$, selects the first persistence coefficient; otherwise, it selects the second persistence.

Therefore, as in the second embodiment, the first persistence coefficient is mapped to the blood flow velocity $V_{current}$ of the most recent frame and is as small as the magnitude of the absolute value of $V_{current}$. The greater the first persistence factor, since the operation more considering the blood flow velocity of the previous frame, persistence calculation unit 108, in the case of using the first persistence coefficient, reduces residual image effect, it is possible to perform an operation to quickly change the blood flow velocity. In contrast, the second persistence coefficient, blood flow velocity V of the previous frame$_{out-1}$ mapped to, and, $V_{out-1}$ for a larger value as the absolute value is large, the second persistence calculation unit 108 in the case of using the stance factor enhances the residual image effect, it is possible to reduce operation changes in blood flow velocity.

Having described various embodiments with reference to the accompanying drawings, the present invention is not limited to these examples. Within the scope of the claims, various modifications or amendments conceivable by those skilled in the art are also included in the technical scope of the present invention. Further, without departing from the scope of the disclosure, it may be any combination of the components in the above embodiment.

In the above embodiment, although processing was performed using the blood flow velocity data included in CFM frame data, in the case where CFM frame data includes data not other than blood flow velocity data $V_{current}$ or $V_{out-1}$ (such as blood flow power data or dispersion data of the blood flow velocity), the persistence calculation unit 108, even with respect to data other than blood flow velocity data, uses the blood flow velocity data for the most recent frame and blood flow velocity data for the frame preceding the most recent frame and the persistence coefficient $C_{persistence}$ and performs a persistence calculation in a similar way as in the above equation (1), and may obtain residual image processed data.

Further, in the above embodiment, it has been performed persistence processing using the blood flow velocity data of the most recent frame and a previous frame, two front, or three or more previous frames of the blood flow velocity data it may be subjected to a persistence processing also be used. Further, not being limited to equation (1), persistence processing may be performed using other calculation equations.

Each functional block employed in the description of the above embodiments are typically implemented as an LSI configured by an integrated circuit having an input terminal and an output terminal. These may be implemented individually as single chips, or may be integrated into one chip including part or all. Although it is referred to here as the LSI, depending on the degree of integration, it may also be called an IC (Integrated Circuit), system LSI, or super LSI.

Further, the method of circuit integration is not limited to the LSI, and may be realized using a dedicated circuit or a general-purpose processor. After manufacturing of the LSI, a programmable FPGA (Field Programmable Gate Array), Reconfigurable Processor (Reconfigurable Processor) connections or settings of circuit cells in the LSI may be utilized.

Furthermore, if, by way of advancements in semiconductor technology or a derivative, an integrated circuit technology comes out to replace LSI's, as a matter of course, it may be used to integrate functional blocks.

The present invention is suitable for a ultrasonic diagnostic apparatus capable of displaying the blood flow velocity.

According to an embodiment, there is provided an ultrasonic diagnostic apparatus which is capable of accurately determining the occurrence of aliasing, and when the aliasing occurs, is capable of adequately correcting for the effect.

Although embodiments of the present invention have been described and illustrated in detail, it is clearly understood that the same is by way of illustration and example only and not limitation, the scope of the present invention should be interpreted by terms of the appended claims.

What is claimed is:

1. An ultrasonic diagnostic apparatus comprising:
    a transceiver that transmits ultrasonic waves by driving a probe repeatedly, receives echoes reflected off a subject, and successively generates a plurality of received signals;
    a color flow mapping signal processing unit that successively generates blood flow velocity data of blood flow in the subject for each frame of a plurality of frames based on the plurality of received signals;
    a residual image processing unit that successively receives the each frame of the plurality of frames and performs residual image processing on blood flow velocity of the each frame;
    the residual image processing unit further comprising;
    an aliasing determination unit that performs a determination of whether or not aliasing occurs in a first blood flow velocity data for a most recent frame of the plurality of frames as received from the color flow mapping signal processing unit and in a second blood flow velocity data for a frame of the plurality of frames immediately preceding the most recent frame that has previously been subjected to the residual image processing; and
    a persistence memory unit that stores the second blood flow velocity data for the frame immediately preceding the most recent frame that has been subjected to the residual image processing of the residual processing unit and a first aliasing determination result that has been determined for the second blood flow velocity data for the frame immediately preceding the most recent frame, wherein the determination by the aliasing determination unit is performed based on the first blood flow velocity data, the second blood flow velocity data, and whether the first aliasing determination result that has been previously determined for the frame immediately preceding the most recent frame indicates presence of aliasing in the blood flow velocity data for the frame immediately preceding the most recent frame that has been subjected to the residual image processing, the aliasing determination unit outputting a second aliasing determination result that is an aliasing determination result of the first blood flow velocity data, and a third aliasing determination result that is an aliasing determination result of the second blood flow velocity data, and a persistence calculation unit that, based on the second and third aliasing determination results and a predetermined persistence coefficient for adjusting the residual image effect, performs a persistence calculation using the first blood flow velocity data and the second blood flow velocity data, outputs a persistence calculation result as a third blood flow velocity data for the most recent frame that is the blood flow velocity data that is subjected to residual image processing, determines whether or not aliasing occurs in the third blood flow velocity data, outputs data which is a fourth aliasing determination result, and outputs the third blood flow velocity data, which is a result of the persistence calculation, and the fourth aliasing determination result to the persistence memory unit.

2. The ultrasonic diagnostic apparatus according to claim 1,
wherein the persistence calculation unit performs the persistence calculation after correcting the blood flow velocity data of the most recent frame and a residual image processed blood flow velocity data of the frame immediately preceding the most recent frame based on the second and third aliasing determination results.

3. The ultrasonic diagnostic apparatus according to claim 1,
wherein the residual image processing unit includes a persistence coefficient determination unit that sets the persistence coefficients based on the second and third aliasing determination results and the first blood flow velocity data.

4. The ultrasonic diagnostic apparatus according to claim 1, the residual image processing unit further comprising:
a frame memory unit that stores the first blood flow velocity data, and
wherein an aliasing determination unit performs aliasing determination on the first blood flow velocity data and the second blood flow velocity data using the first aliasing determination result, which are obtained from the frame memory unit and the persistence memory unit respectively.

5. The ultrasonic diagnostic apparatus according to claim 1, wherein the aliasing determination unit determines whether or not aliasing occurs in the first blood flow velocity data and the second blood flow velocity data based on a result of comparing magnitudes of the first blood flow velocity data and second blood flow velocity data with a predetermined threshold value, and the first aliasing determination result.

6. The ultrasonic diagnostic apparatus according to claim 1, the residual image processing unit further comprising:
a first persistence coefficient determination unit that sets a first persistence coefficient based on the second and third aliasing determination results and the first blood flow velocity data;

a second persistence coefficient determination unit that sets a second persistence coefficient based on the second and third aliasing determination results, and the second blood flow velocity data;

a first persistence calculation unit that performs a persistence calculation using the first blood flow velocity data and second blood flow velocity data based on the second and third aliasing determination results and the first persistence coefficient;

a second persistence calculation unit that performs a persistence calculation using the first blood flow velocity data and second blood flow velocity data based on the second and third aliasing determination results and the second persistence coefficient;

a maximum value selection unit that compares absolute values of calculation results outputted from the first and second persistence calculation units, whereby a larger calculation result is outputted as the third blood flow velocity data, determines whether or not aliasing occurs in the third blood flow velocity data, and outputs a fourth aliasing determination result that is an aliasing determination result thereof.

7. The ultrasonic diagnostic apparatus according to claim 1, the residual image processing unit further comprising:
a first persistence coefficient determination unit that sets a first persistence coefficient based on the second and third aliasing determination results and the first blood flow velocity data;

a second persistence coefficient determination unit that sets a second persistence coefficient based on the second and third aliasing determination results, and the second blood flow velocity data, and a persistence coefficient selection unit that compares an absolute value of the first blood flow velocity data with an absolute value of the second blood flow velocity data, and selects the first persistence coefficient when the absolute value of the first blood flow velocity data is larger and otherwise selects the second persistence coefficient, wherein the persistence calculation unit performs a persistence calculation using the first blood flow velocity data and the second blood flow velocity data based on the second and third aliasing determination results and the selected persistence coefficient.

\* \* \* \* \*